(12) United States Patent
Bau et al.

(10) Patent No.: US 7,964,159 B2
(45) Date of Patent: Jun. 21, 2011

(54) NANOTUBE-BASED SENSORS AND PROBES

(75) Inventors: Haim H. Bau, Swarthmore, PA (US); Byong Man Kim, East Brunswick, NJ (US); Michael A. Riegelman, Bethesda, MD (US); Yury Gogotsi, Ivyland, PA (US)

(73) Assignees: The Trustees Of The University of Pennsylvania, Philadelphia, PA (US); Drexel University, Philadelphia, PA (US)

( * ) Notice: Subject to any disclaimer, the term of this patent is extended or adjusted under 35 U.S.C. 154(b) by 1020 days.

(21) Appl. No.: 11/177,111

(22) Filed: Jul. 8, 2005

(65) Prior Publication Data

US 2007/0009379 A1 Jan. 11, 2007

(51) Int. Cl.
*G01N 21/01* (2006.01)
*G01N 21/75* (2006.01)
*G01N 33/48* (2006.01)

(52) U.S. Cl. ......... 422/425; 422/68.1; 422/83; 977/920; 977/924

(58) Field of Classification Search .................... 422/50, 422/55, 57, 58, 68.1, 83, 425; 977/902, 904, 977/906, 920, 923, 924, 925
See application file for complete search history.

(56) References Cited

U.S. PATENT DOCUMENTS
2003/0207326 A1* 11/2003 Su et al. ..................... 435/7.1

OTHER PUBLICATIONS

T. Ito et al., Observation of DNA Transport Through a Single Carbon Nanotube Channel Using Fluorescence Microscopy, Chem. Commun. 1482-1483 (2003).*
Riegelman, Dielectrophoretic Assembly and Integration of Nanofluidic Devices (Masters Thesis), University of Pennsylvania (2004).*
R. Karnik et al., Electrostatic Control of Ions and Molecules in Nanofluidic Transistors, 5 Nano Letters 943-948 (2005).*
R. R. Henriquez et al., The Resurgence of Coulter Counting for Analyzing Nanoscale Objects, 129 Analyst 478-482 (2004).*
Bau, H.H., et al., "Fabrication of nanofluidic devices and the study of fluid transport through them," *Proceed. of SPIE*, 2004, Lai, W.Y.-C., et al. (Eds.), 201-213 (abstract 1 page).
Berg, M., et al., "Development and characterization of temperature-controlled microreactors for protein crystallization," *Acta Cryst.*, 2002, D58, 1643-1648.
Bradley, J.-C., et al., "Nanotubes synthesis using alumina template (a4)," *CPS: Chemistry/0303002*, downloaded Mar. 27, 2003, 6 pages, http://preprint.chemweb.com/chemistry/0303002.
Che, G., et al., "Chemical vapor deposition based synthesis of carbon nanotubes and nanofibers using a template method," *Chem. Mater.*, 1998, 10, 260-267.

(Continued)

*Primary Examiner* — Glenn Caldarola
*Assistant Examiner* — Randy Boyer
(74) *Attorney, Agent, or Firm* — Woodcock Washburn LLP

(57) ABSTRACT

Described herein are novel devices for the study of transport characteristics of complex or simple fluids, interactions among molecules in suspension, interactions between molecules in suspension and wall-bound molecules, and biochemical sensing devices made of reservoirs for fluid containment linked by a nanotubes. Also disclosed are methods of delivering medicaments and monitoring fluidic interactions of molecules or analytes.

67 Claims, 15 Drawing Sheets

OTHER PUBLICATIONS

DeRose, J.A., et al., "A comparative study of colloidal particles as imaging standards for microscopy," *J. of Microscopy*, 1999, 195(Pt. 1), 64-78.

Duff, D.G., et al., "A new hydrosol of gold clusters. 1. Formation and particle size variation," *Langmuir*, 1993, 9, 2301-2309.

Duval, J.F.L., et al., "Faradaic depolarization in the electrokinetics of the metal-electrolyte solution interface," *J. of Colloid & Interface Sci.*, 2003, 260, 95-106.

Frens, G., Controlled nucleation for the regulation of the particle size in monodisperse gold suspensions, *Nature Physical Science*, 1973, 241, 20-22.

Gogotsi, Y., et al., "In situ multiphase fluid experiments in hydrothermal carbon nanotubes," *Appl. Phys. Lett.*, 2001, 79(7), 1021-1023.

Gogotsi, Y., et al., "Carbon nanopipes for nanofluidic devices and In-situ fluid studies," *NSF Nanoscale Sci. & Eng. Grantees Conf.*, 2003, 3 pages.

Ito, T., et al., "Simultaneous determination of the size and surface charge of individual nanoparticles using a carbon nanotube-based coulter counter," *Anal. Chem.*, 2003, 75, 2399-2406.

Kim, B.M., et al., "Optical microscope study of liquid transport in carbon nanotubes," *Nano Lett.*, 2004, 4(11), 2203-2208.

Kim, B.M., et al., "Filling carbon nanotubes with particles," *Nano Lett.*, 2005, 5(5), 873-878.

Kim, B.M., et al., "The fabrication of integrated carbon pipes with sub-micron diameters," *Nanotechnology*, 2005, 16, 1317-1320.

Kluijtmans, S.G.J.M., et al., "Dynamics of uncharged colloidal silica spheres confined in bicontinuous porous glass media," *Langmuir*, 1997, 13, 4982-4987.

Knitter, R., et al., "Ceramic microreactors for heterogeneously catalysed gas-phase reactions," *Lab Chip*, 2004, 4, 378-383.

Miller, S.A., et al., "Electroosmotic flow in template-prepared carbon nanotube membranes," *J. Am. Chem. Soc.*, 2001, 123, 12335-12342.

Parthasarathy, R.V., et al., "Template synthesis of graphitic nanotubules," *Adv. Mater.*, 1995, 7(11), 896-897.

Peterson, D.S., et al., "Enzymatic microreactor-on-a-chip: protein mapping using trypsin immobilized on porous polymer monoliths molded in channels of microfluidic devices," *Anal. Chem.*, 2002, 74, 4081-4088.

Reed Business Information, *Micro Nano*, 2004, 9(22), p. 20.

Riegelman, M., et al., "Nanofabrication of carbon nanotube (CNT) based fluidic device," *Proceed. of NATO-ASI Nanoengineered Nanofibrous Materials*, Guceri, S., et al. (Eds.), The Netherlands, 2004, 407-414.

Riegelman, M.A., "Dielectrophoretic assembly and integration of nanofluidic devices," Master's Thesis, *University of Pennsylvania*, 2004, ii-iv, 1-87.

Rossi, M.P., et al., "Environmental scanning electron microscopy study of water in carbon nanopipes," *Nano Lett.*, 2004, 4(5), 989-993.

Saleh, O.A., et al., "Quantitative sensing of nanoscale colloids using a microchip coulter counter," *Rev. of Scientific Instruments*, 2001, 72(12), 4449-4451.

Spherotech, Inc., *III. Product and Price Information; 1. SPHERO™ Polystyrene Particles*, http://spherotech.com/PolParIn.pdf, downloaded Jul. 12, 2005, 4-7.

Stöber, W., et al., "Controlled growth of monodisperse silica spheres in the micron size range," *J. of Colloid & Interface Sci.*, 1968, 26, 62-69.

Sun, L., et al., "Single carbon nanotube membranes: a well-defined model for studying mass transport through nanoporous materials," *J. Am. Chem. Soc.*, 2000, 122, 12340-12345.

Sun, L., et al., "Fabrication and characterization of single pores for modeling mass transport across porous membranes," *Langmuir*, 1999, 15, 738-741.

Supple, S., et al., "Rapid imbibition of fluids in carbon nanotubes," *Phys. Rev. Lett.*, 2003, 90(21), 214501-1-214501-4.

Wagner, J., et al., "Generation of metal nanoparticles in a microchannel reactor," *Chem. Eng. J.*, 2004, 101, 251-260.

Watts, P., et al., "Microfluidic combinatorial chemistry," *Curr. Opinion in Chem. Biol.*, 2003, 7, 380-387.

Yamamoto, T., et al., "PDMS-glass hybrid microreactor array with embedded temperature control device. Application to cell-free protein synthesis," *Lab Chip*, 2002, 2, 197-202.

B. Kim and H.H. Bau, 2005, Hybrid fabrication of Carbon Nanotube-Based Devices and the Measurement of Ionic Current Through Them, No. 0394, TAS (Micro Total Analysis Systems) Conference 2005, Boston, Massachusetts, USA, Oct. 9-13, 2005, 2 pages.

* cited by examiner

NANOTUBE-BASED SENSORS AND PROBES

STATEMENT OF GOVERNMENT INTEREST

This invention was made with government support under grant number CTS-0210579, awarded by the National Science Foundation (NSF). The government has certain rights in the invention.

FIELD OF THE INVENTION

The present invention relates to nanotube based sensors and probes used for biochemical and chemical sensing and processing and for electron and optical microscopy of chemical and biological interactions in liquids and gases. Also disclosed are methods of medicament transportation and monitoring molecular interactions.

BACKGROUND OF THE INVENTION

One of the obstacles encountered when studying nanoscale phenomena is the limited resolution of visible light. When dealing with solid or frozen materials, one can take advantage of the relatively small wavelengths of electrons to visualize phenomena at sub-nanometer length scales. Unfortunately, however, conventional electron microscopy requires vacuum conditions, and, in the past, this has precluded its use for the study of volatile fluids. With present day technology, at best, one can operate with environmental chambers that allow the introduction of humid gases. The conditions prevailing in the environmental chamber are very different from the ones experienced, for example, by biological molecules in aqueous solutions and catalytic reactions in general. This limits one's ability to carry out studies of biological interactions and chemical reactions under controlled conditions.

It is envisioned that experiments currently conducted with near field microscopy and total internal reflection (TIRF) microscopy can be duplicated with electron microscopy with much higher resolution than is currently feasible. The molecules to be observed can be tagged with particles, atoms, and possibly observed directly without a label. As a result, various reactions and interactions in liquid and gaseous environments may be studied.

A common method for the detection of particles and biological substances is to transmit the analyte through a small tube or pore and monitor the effect of the presence of the analyte on the ionic current. The presence of an analyte suppresses or blocks the ionic current. The magnitude of the blockage and its duration can be used to characterize the size of the analyte. To make the detection process specific, one can use functionalized carriers such as particles or known molecules that bind the analyte specifically and monitor the effect of the analyte on the characteristics of the carrier. The sensitivity of this biosensing technique depends on the size of the pore or tube. The small diameter of the nanotubes would facilitate the construction of high sensitivity devices.

Currently, pulled glass micropipettes are used to study the properties of cells and to exchange material with a cell's interior. These techniques are intrusive and typically limited to operating with a single cell at a time. There is a need for less intrusive probes.

Currently scanning probes allow one to probe the mechanical and electrical properties of samples. There is an unmet need for probes that can exchange fluids and molecules with the scanned sample.

SUMMARY OF THE INVENTION

The present invention provides analytical devices comprising a substrate, a barrier structure defining two reservoirs for fluid containment, and at least one nanotube between the reservoirs, the lumen of which nanotube is at least partially observable by electron, optical, or ion beam microscopy, and the openings of which nanotube are in fluid communication with said reservoirs.

The techniques described herein facilitate the fabrication of devices comprising a plurality of nanotubes similarly or differently sized. The nanotubes may also be similarly or differently functionalized to interact with the same or different reservoirs. Groups of nanotubes may communicate with shared reservoirs or with individual reservoirs.

The present invention also includes methods of monitoring the fluidic interactions of molecules. The method comprises placing the molecules in a fluid, placing the fluid into a device of the present invention, causing the fluid to flow from one reservoir to another reservoir through the nanotube, and observing the fluidic interaction of the molecules within the nanotube.

Also disclosed are cellular or scanning probes comprising a substrate, a barrier structure on the substrate defining a reservoir for fluid containment, and a nanotube. The nanotube has an opening proximal to and in fluid communication with the reservoir and the distal opening of the nanotube is exposed. There are also embodiments in which the distal opening is used for insertion into a biological membrane. Such embodiments may facilitate the introduction into or withdrawal from a cell or molecule in fluids.

There are also methods of delivery for a medicament comprising placing a medicament in a fluid, then placing that fluid into at least one probe or device of the present invention, and then delivering the medicament contained within the fluid into a biological membrane through the nanotube.

Arrays comprising more than one cellular or scanning probe are disclosed. The arrays comprise a substrate and barrier structures on said substrate defining reservoirs for fluid containment. They also comprise nanotubes having openings proximal to and in fluid communication with the reservoirs and openings distal to the reservoirs for insertion into a biological membrane. More than one probe may be located on the same substrate.

The fabrication techniques described herein facilitate the fabrication of devices that allow a plurality of probes of different sizes and functionalization to interact with a single or group of cells. Groups of probes may communicate with shared reservoirs or with individual reservoirs.

BRIEF DESCRIPTION OF THE DRAWINGS

FIG. 16B is a cross-section view depicting an array of probes with more than one tube interacting with cells.

DETAILED DESCRIPTION OF ILLUSTRATIVE EMBODIMENTS

Disclosed herein are hybrid methods for the fabrication of nanotube-based fluidic devices, devices for biochemical sensing and processing, and devices that facilitate electron microscopy of biological and chemical interactions in liquids or pressurized gases. The embodiments of the present invention allow for the transport of simple and complex fluids from one reservoir to the other or to a biological membrane through a nanotube. The transportation may be facilitated by means of an electric field across the electrodes, such as by electroosmosis or electrophoresis, by electro-wetting and electro-migration and by diffusion. The fluids may also be made to flow by surface tension or pressure. Molecules may be transmitted by the directed motion of cargo carrying, processive molecular motors. The activity inside the nanotube may be observed through a pathway in the substrate and between the reservoirs to the lumen of the nanotube. The contents of the nanotube may be observed, for example, with optical, fluorescent, and electron microscopes or ion-beam microscopes. Alternatively, they can be measured with electrical means such as the monitoring of the ionic current through the liquid confined inside the nanotube and the monitoring of the effect of the contents on the nanotube wall's electrical, optical, and mechanical properties.

One embodiment that may be preferred provides devices comprising a substrate; a barrier structure defining two reservoirs for fluid containment; and a nanotube between the reservoirs. The openings of the nanotube are in fluid communication with the reservoirs. The term "reservoirs," as used herein, is considered a chamber and its interior used for storing fluid or a conduit that facilitates the supply of fluids. The nanotube connects the two reservoirs and facilitates the transport of fluids from one reservoir to the other. Such an embodiment may be utilized as a biosensor for the detection and characterization of molecules, as a device to study the transport characteristics of simple and complex confined liquids. Some embodiments may be used as a miniature containment vessel allowing for electron microscopy of reactions and interactions in liquids and pressurized gases within the vacuum environment of the electron microscope.

Figure 1:
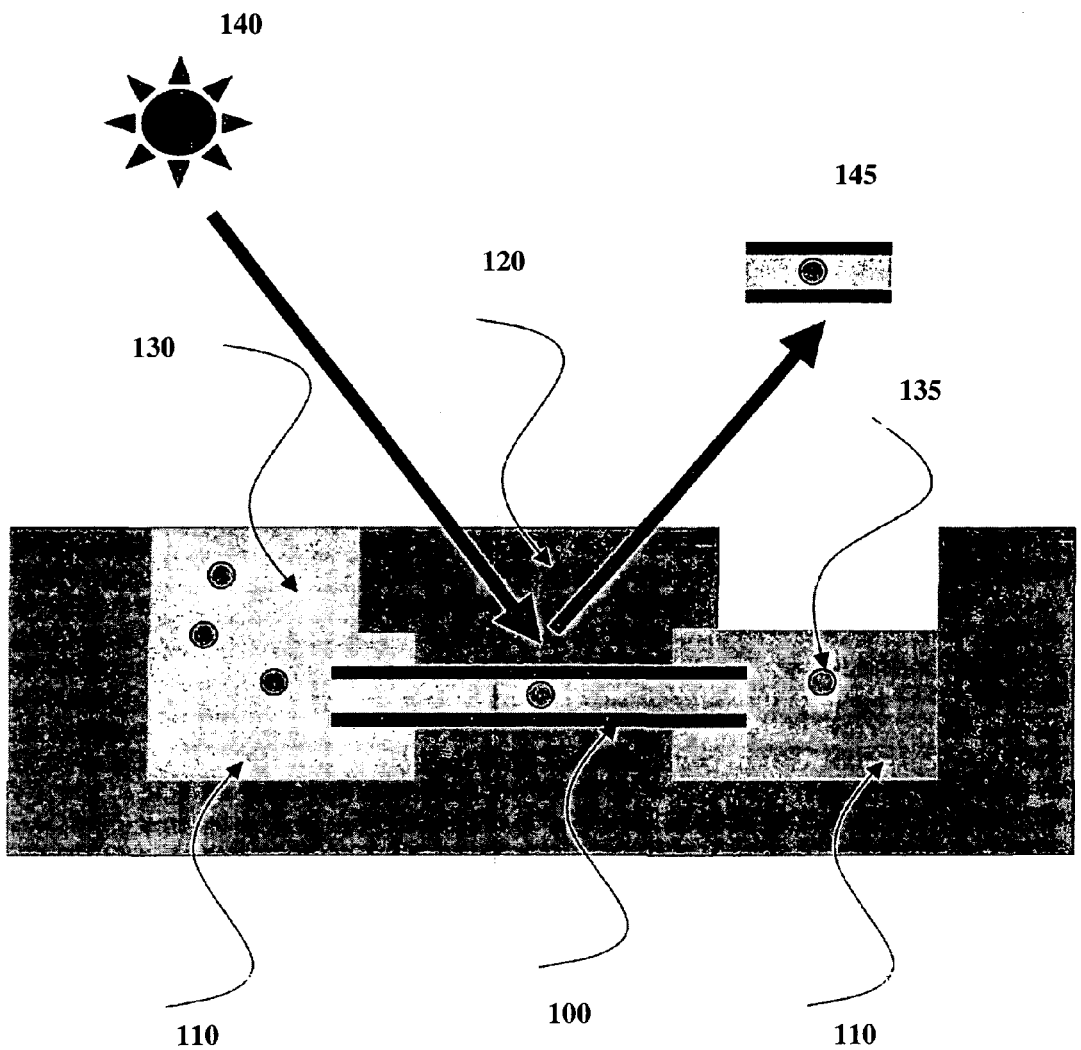
FIG. 1 illustrates a cross-section of an embodiment of the current invention.

FIG. 1 depicts the cross-section of an embodiment of the present invention. The device consists of a nanotube conduit 100, two reservoirs 110, and a barrier structure 120. The barrier structure 120 separates the reservoirs 110 and prevents fluid leakage between them while holding the nanotube 100 in position and insuring that fluid transport occurs though the nanotube 100. The barrier structure 120 may consist of either a single barrier or two barriers 120 as in FIG. 7. In the latter case, the nanotube 100 wall is exposed to minimize interference with various observation techniques, such as electron, optical, or fluorescence microscopy. One or both of the reservoirs may hold a fluid 130, which may comprise liquids, suspensions, emulsions, or gases or a combination thereof. The suspensions may comprise particles 135 such as fluorescent beads, functionalized beads, unfunctionalized beads, magnetic beads, or macromolecules or a combination thereof. The macromolecules may comprise nucleic acids, enzymes, dendrimers, or proteins, or a combination thereof. The reservoirs may be open or capped and may be capped with polymer, semiconductor, glass, or metal. An optical source 140, such as a visible light or a fluorescence light, may be used to see through the walls of the nanotube 100 to detect the motion of the fluid, the substance, and the interactions among molecules inside the nanotube 100. The current-voltage technique may also be used to characterize the fluid motion inside the nanotube 100 and to detect the presence and size of the particles 135 or molecules.

Figure 2:
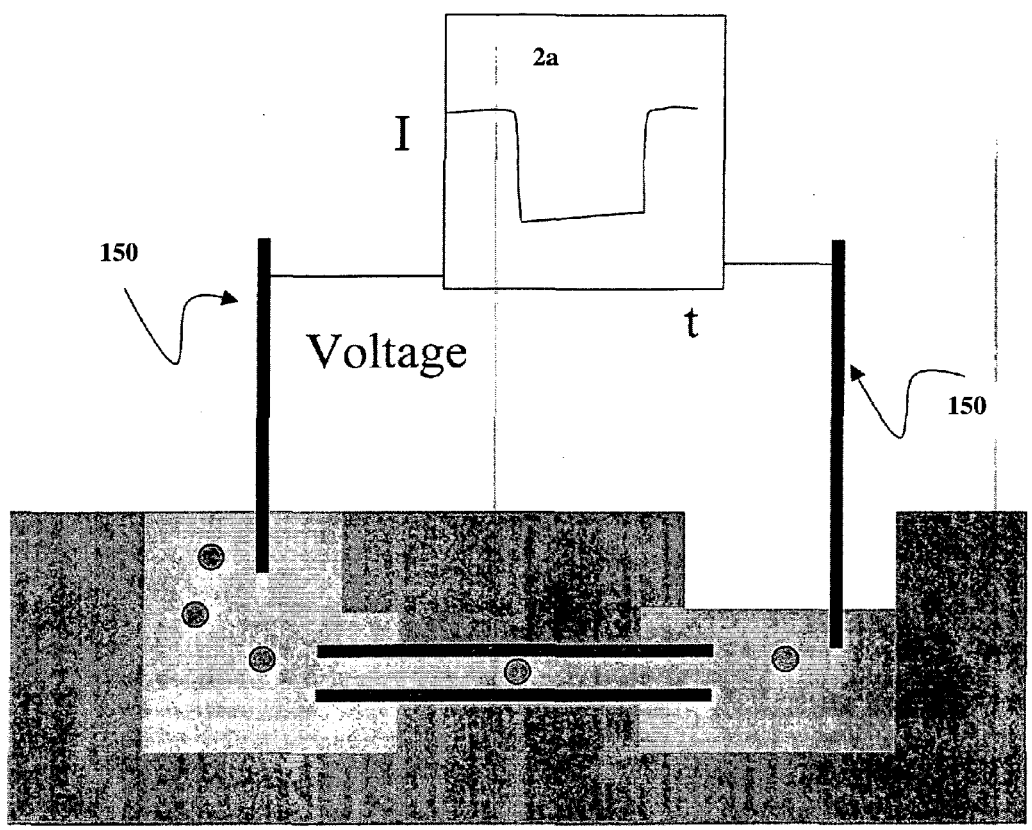
FIG. 2 illustrates a cross-section of an embodiment with a voltage applied between two electrodes.

FIG. 2 depicts embodiments where the reservoirs 110 comprise electrodes 150. A voltage is applied between the electrodes 150 and the ionic current (I) of the fluid medium across the nanotube 100 is measured as a function of time. The amplitude of the ionic current suppression or blockage is proportional to the size of the particle 135 or molecule translocating through the nanotube 100. A graphic of the anticipated current measurement as a function of time, t, is depicted in the FIG. 2 inset.

Figure 3:
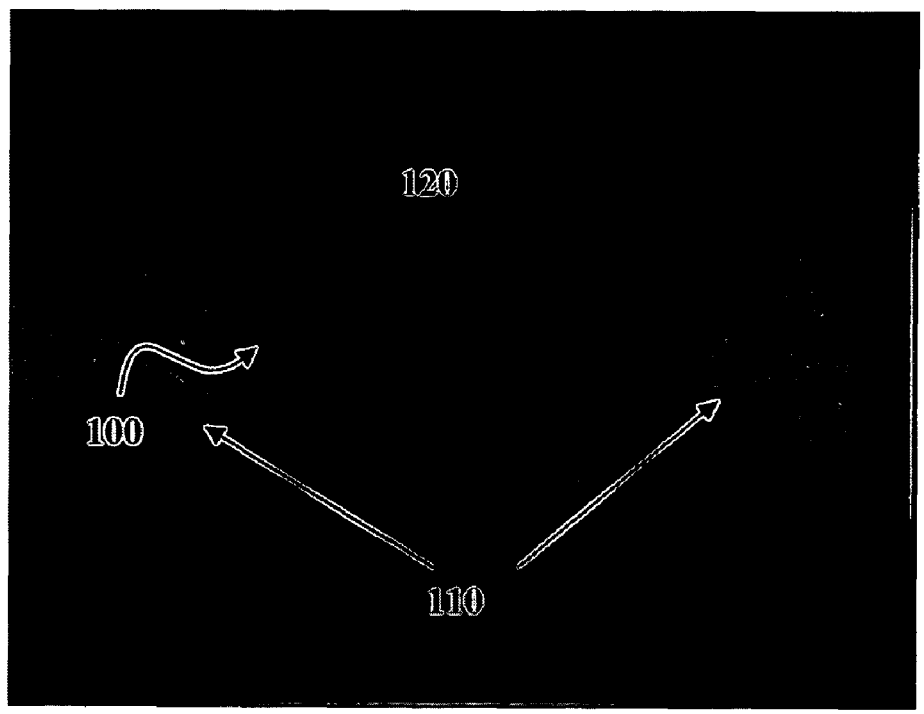
FIG. 3 is an optical microscope image of an embodiment of the present invention.

FIG. 3 shows an optical image of an embodiment of the present invention. This embodiment was built based on the process steps a-h depicted in FIG. 4. The device fabrication starts with a substrate 160. The substrate may be a silicon wafer. The substrate may comprise silicon, glass, plastic, or polymer. Two electrodes 150 are placed on the substrate using standard techniques. The electrodes 150 may be placed with a NiCr wetting layer and patterned on the substrate using standard microfabrication techniques (step b). A nanotube 100, such as a carbon nanotube, is between the electrodes 150 with a dielectrophoresis assembly method (step c). The nanotubes of the present invention may also comprise silicon, silicon oxide, semiconductor, metal, or glass. Next, the nanotube ends are capped with a micropatterned sacrificial layer 170 such as that formed with a positive photoresist (S1813), using standard microfabrication techniques (step d). Then, a thick organic polymer 190 is spun (step e) and patterned to open the reservoirs 110 and to form the barrier structure 120 using standard microfabrication techniques (step f). The barrier structure 120 comprises polymer, silicon, or silicon dioxide. A weak oxygen plasma or HF acid treatment may be applied between steps d and e to promote the adhesion of SU8 to the surface of the substrate 160 or to the nanotube 100 surface. The sacrificial layers 170 are removed, using a solvent such as a SU-8 developer or acetone, to expose the nanotube 100 ends (step g).

Figure 7:
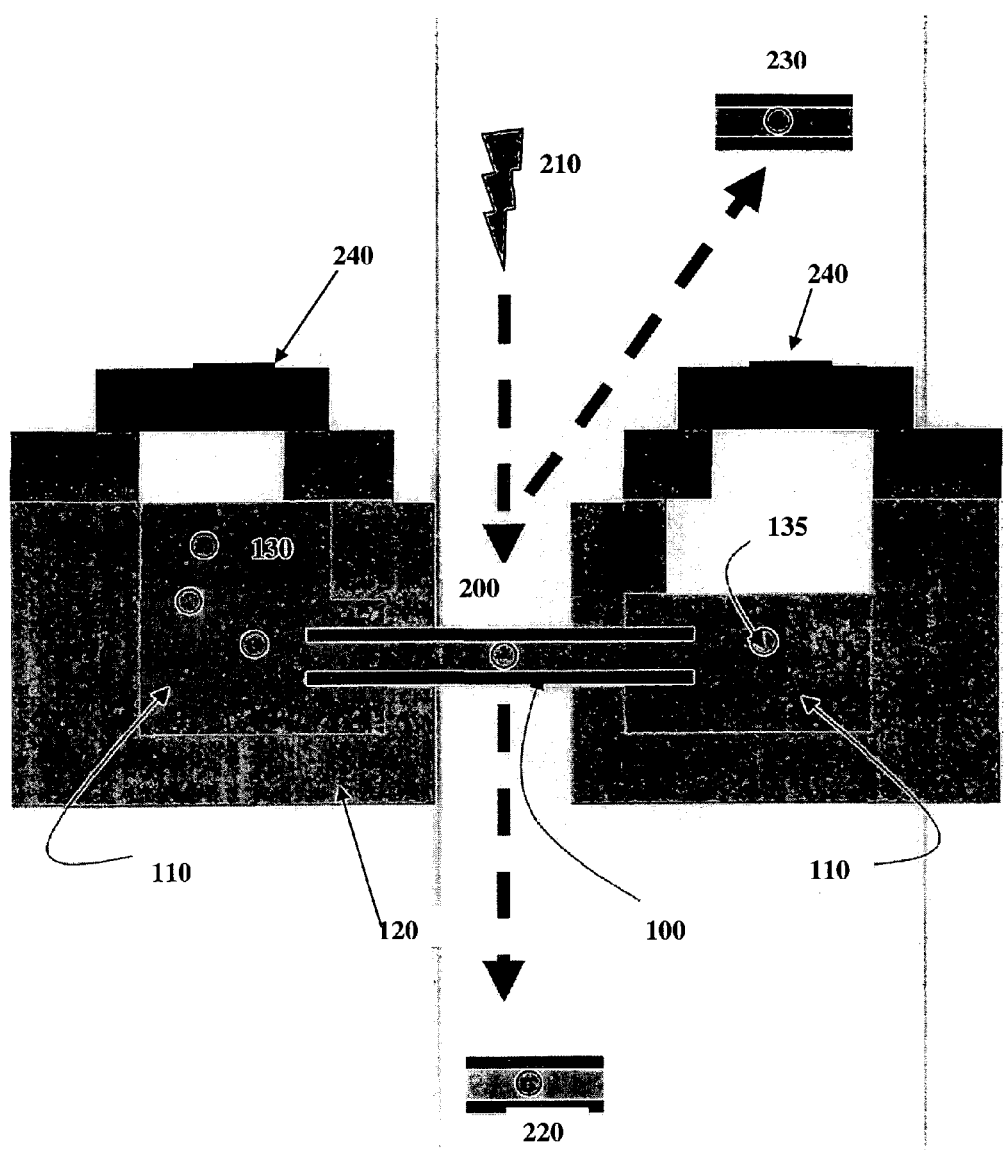
FIG. 7 illustrates a cross-section of an embodiment of the invention in which there is a pathway between the reservoirs to the nanotube.

For some embodiments, additional steps may be incorporated to cap the reservoirs 110 with a cover layer structure 240 as seen in FIG. 7. A cover structure 240 formed of a glass slide with pre-drilled access holes and coated with a thin layer of an adhesive film like SU8, may be placed on the finished sensor device. The cover may also be formed with a polymer or elastomer layer.

In other embodiments, the biochemical sensor may further comprise a pathway 200 through said polymer and between said reservoirs 110 to the lumen of said nanotube 100. This pathway allows for the contents of the nanotube 100 to be observed using microscopy known in the art. FIG. 7 depicts the cross-section of one embodiment of the present invention. The biochemical sensor comprises a nanotube 100 two reservoirs 110, and an air pathway 200. The reservoirs 110 are separated by the air pathway 200 and bridged by the nanotube 100. The reservoirs 110 may be filled with a fluid 130 or with fluid comprising particles or macromolecules 135. The air pathway 200 provides a route for a beam of electrons 210 to reach the nanotube 100. Electron microscope observations can be carried out either in transmission 220 or reflection 230 modes. An optical or fluorescent source 140 may also be used to visualize the fluid and particle motions inside the nanotube 100 using either transmission 220 or reflection 230 modes. The current-voltage technique, shown in FIG. 8, may also be used to characterize the fluid motion inside the nanotube 100 and to detect the presence and size of particles and molecules. In this case, voltage is applied between the electrodes 150 and the ionic current (I) of the fluid medium in the nanotube 100 is measured as a function of time. The amplitude of the ionic current's suppression or blockage is proportional to the size of the particle or molecule translocating through the nanotube 100. A depiction of the anticipated current measurement as a function of time, t, is depicted in the Figure inset.

Figure 9:
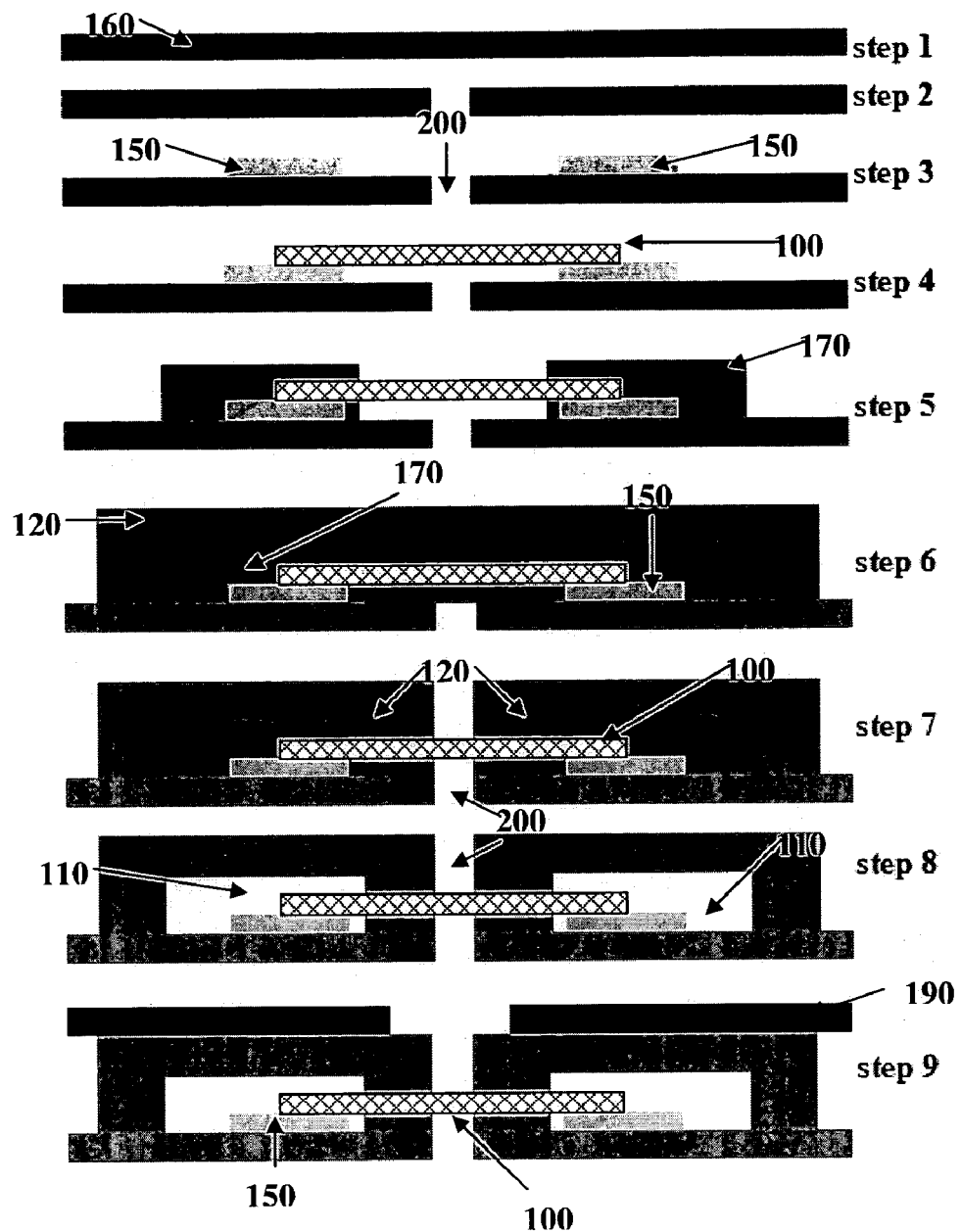
FIG. 9 illustrates a method of making another embodiment of the invention with a pathway for electrons, light, and other means of visualization.

The embodiment depicted in FIG. 7 may be constructed according to process steps 1-9 depicted in FIG. 9. The device fabrication starts with a substrate 160. The pathway 200 in the substrate 160 is formed with wet chemical etching. One can employ KOH etching, ion-beam etching using a focused ion beam or a combination of the two. Two electrodes 150 are formed on the substrate 160 using standard microfabrication processes. A nanotube 100 is between the electrodes 150 and across the pathway 200 by using a dielectrophoresis assembly method. Next, the nanotube ends are capped with a micropatterned sacrificial layer 170 such as that formed by a positive photoresist using standard microfabrication processes. The device is spun on with a thick photoresist 190 and then patterned to open access to the reservoirs 110 using standard microfabrication processes. A weak oxygen plasma or HF acid treatment of the device between steps 5 and 6 may be applied to improve the adhesion of the thick SU8 to the substrate 160 or to the nanotube 100 surface. The sacrificial layers 170 are removed using a solvent, like SU8 developer or acetone, to expose the nanotube 100 ends to air.

Additional steps may be incorporated to add a cover structure 240. Two approaches are described. A cover structure 240, formed of a glass slide with pre-opened windows 250 and spun on one side of the structure with a thin layer of adhesive film may be used to make the embodiment as shown in step 9. The cover structure 240 structure may also be introduced at step 7 prior to opening of the reservoirs using standard microfabrication processes. Inlet and outlet ports may be sealed off with properly engineered closures to make the devices vacuum tight.

Figure 10:
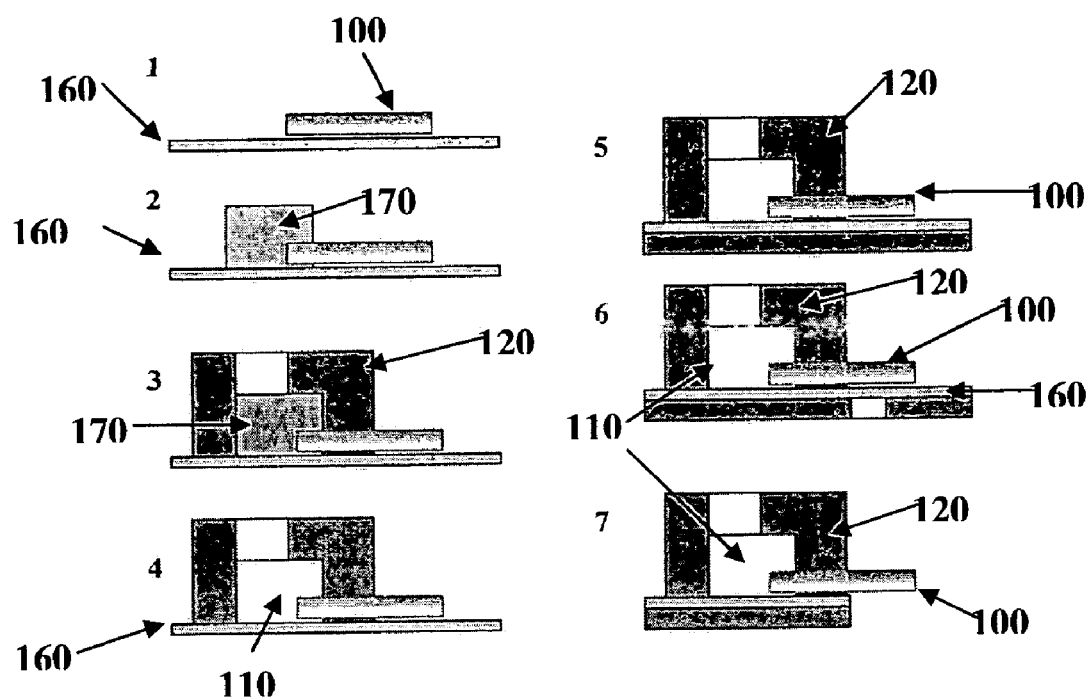
FIG. 10 illustrates steps that may be used in making a nanotube-based probe of the present invention.

In addition to the applications listed above, there are embodiments used as scanning or cellular probes to penetrate biological membranes to exchange material, deliver material, or extract material with minimal intrusion and high resolution and serve as a nanoelectrode. FIG. 10 depicts the cross-section and the front view of such an embodiment. Such embodiments of the present invention comprise a substrate 160; a barrier structure 120 defining one reservoir 110 for fluid containment; and a nanotube 100 having an opening proximal to and in fluid communication with the reservoir 110 and an opening distal to the reservoir 110 being exposed. The scanning probes of the present invention comprise a substrate 160; a barrier structure 120 on the substrate 160 defining one reservoir for fluid containment; and a nanotube 100 having an opening proximal to and in fluid communication with the reservoir 110 and an opening distal to the reservoir for insertion into a biological membrane.

The exposed opening of the nanotube 100 that is distal to the reservoir is for insertion into a biological membrane. Once inserted, a sample may be retrieved from the membrane so that it may be observed or analyzed within the nanotube 100 or reservoir 110. In other embodiments, once the distal opening of the nanotube 100 is inserted, the contents of the reservoir 110 may be injected into the membrane. The scanning probes may be functionalized to facilitate selective binding and transport. There are embodiments that may also serve as nanoelectrodes.

Figure 15A:
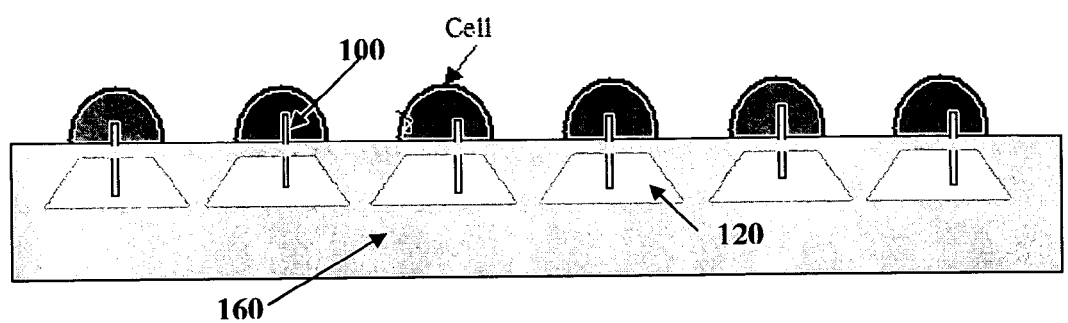
FIGS. 15A and 15B are schematics of arrays interacting with cells.
Figure 15B:
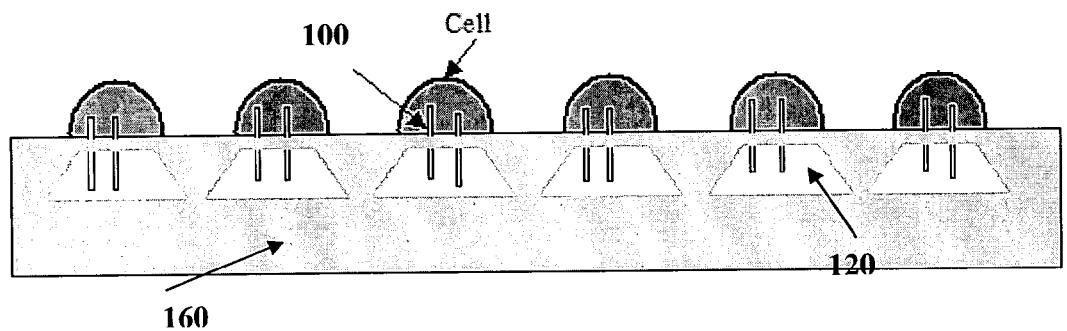
Figure 16:
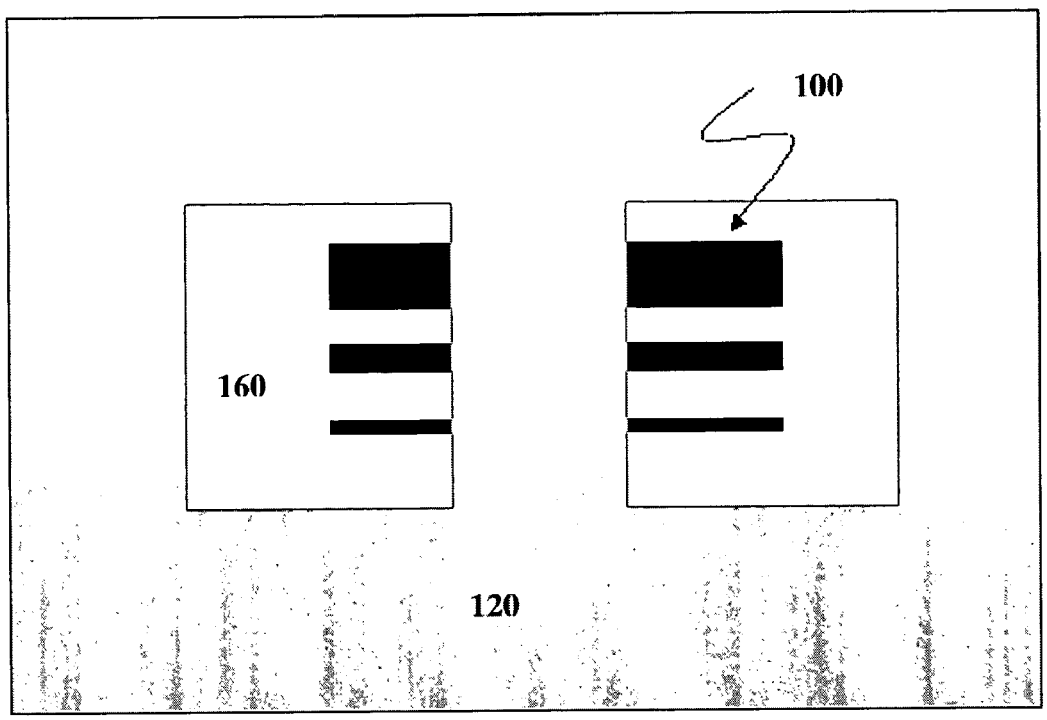
FIG. 16 is a plane-view depiction of an embodiment comprising multiple nanotubes of different diameters and connecting the two reservoirs.

Multiple probes may make an array. The probes may communicate, in parallel, with multiple cells for massive parallel processing. Such an embodiment may be seen in FIGS. 15A, and 15B. Such arrays comprise more than one probe comprising a substrate and a barrier structures on said substrate comprising reservoirs for fluid containment. The nanotubes have openings proximal to and in fluid communication with the reservoirs and openings distal to the reservoirs for insertion into a biological membrane. More than one probe in such embodiments is located on the same substrate. More than one nanotube may have an opening proximal to the reservoir. The fluids held in such reservoirs may differ. Embodiments may be used for drug screening and genetic and tissue engineering. Furthermore, there are biochemical sensing devices comprising a scanning probe as described herein.

The cellular probes of the present invention may be smaller or have a higher aspect ratio (i.e. the ratio of the tip's length to its width) than probes currently used. There may be a plurality of probes with individual nanotubes or groups of nanotubes communicating with individual cells. Some embodiments may comprise nanotubes connected to microfluidic conduits for continuous supply of reagents.

Some embodiments of the probes of the present invention may be constructed according to process steps 1-7 illustrated in FIG. 10. The embodiment may be made starting with a substrate 160. Two electrodes, such as Au electrodes with a NiCr wetting layer, are formed on the substrate using standard microfabrication techniques. A nanotube 100 is placed in position between the electrodes 150 using a dielectrophoresis assembly method. Next, one of the nanotube 100 ends is capped with a micro patterned sacrificial layer 170 formed from positive photoresist (S1813) using standard microfabrication processes. Thick permanent photoresist 190 is then spun on both sides of the wafer, patterned, and developed. A weak oxygen plasma or HF acid treatment of the device between steps 2 and 3 may be applied to improve the adhesion of the thick SU8 to the substrate's or to the nanotube 100 surface. The sacrificial layers are removed using a solvent, such as a SU8 developer or acetone, to form the reservoir 110. Finally, part of the substrate is etched away, leaving a chamber with a protruding nanotube 100.

Figure 11:
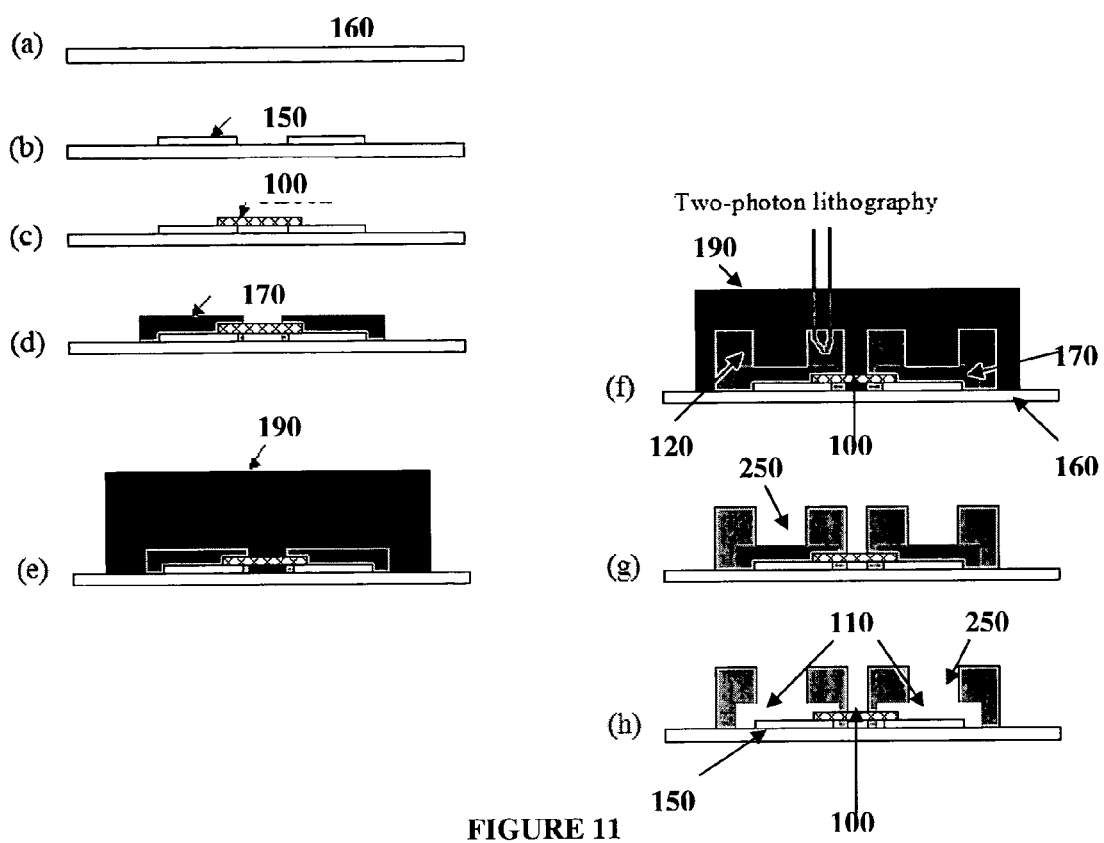
FIG. 11 illustrates steps that may be used to fabricate a nanotube fluidic device with two photon technique.
Figure 12:
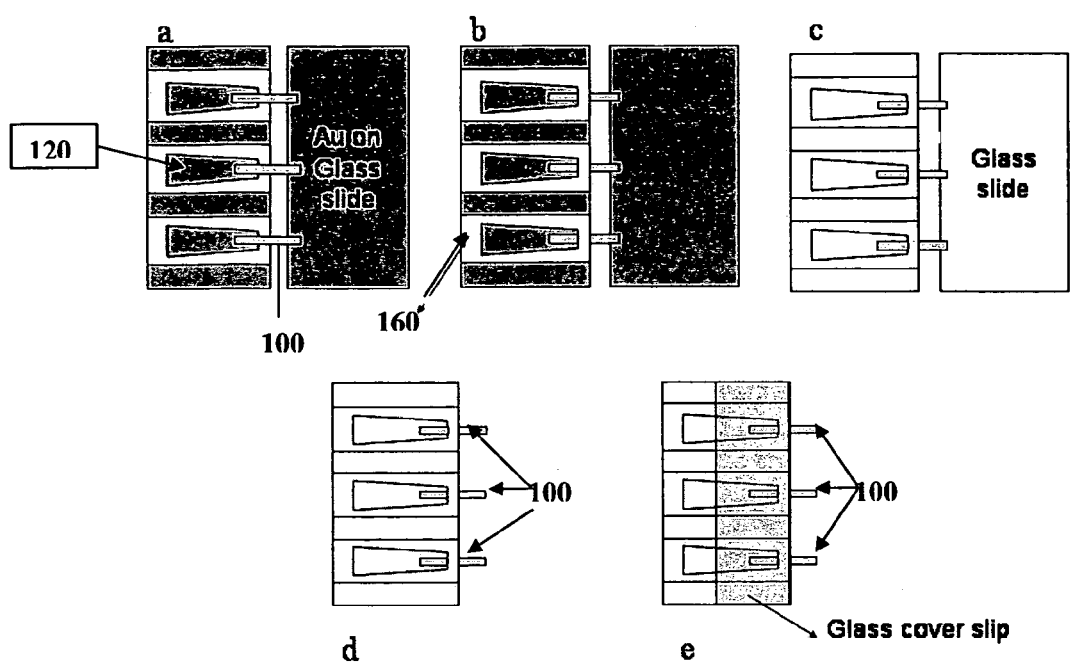
FIG. 12 illustrates the steps that can be used to fabricate a device that consists of a plurality of probes for parallel interactions.
Figure 13:
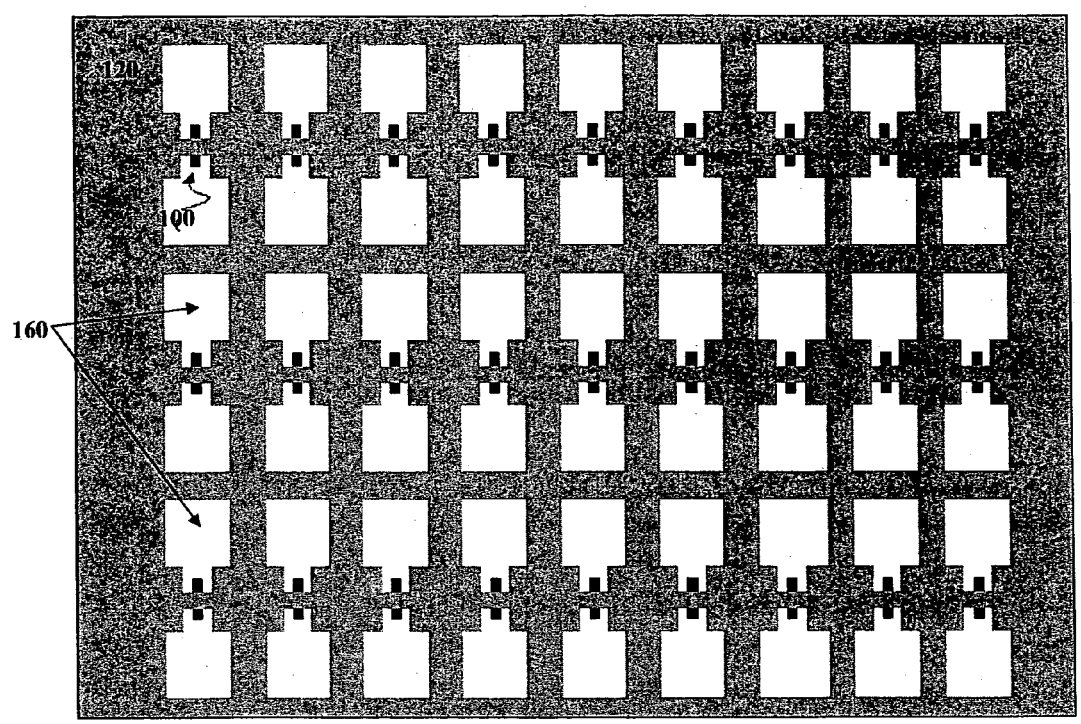
FIG. 13 illustrates a schematic plane-view depiction of array of the present invention as seen from the step (g) of FIG. 4.
Figure 14:
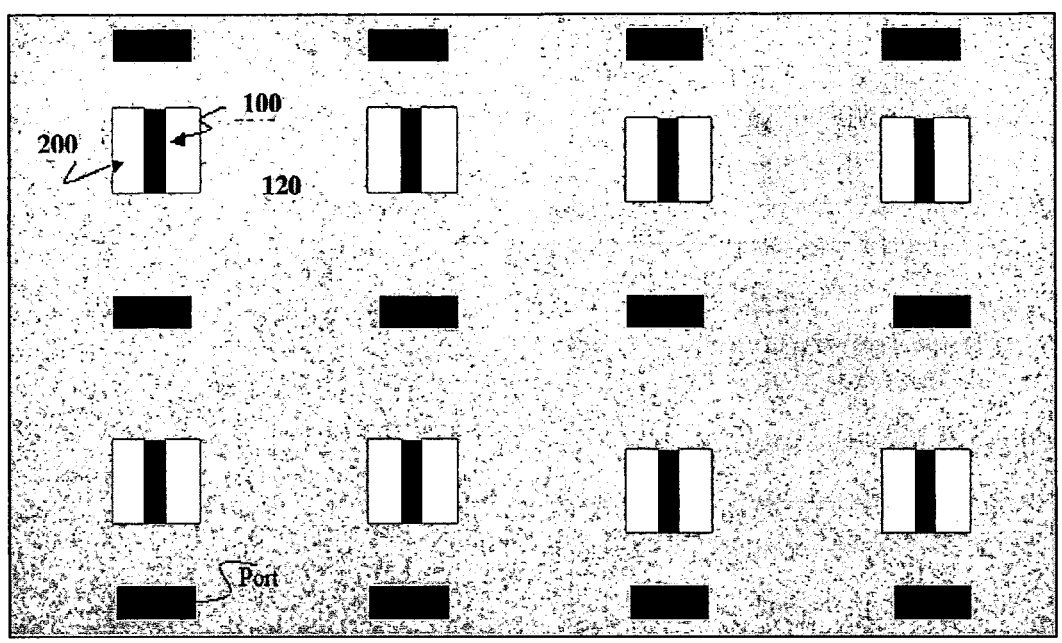
FIG. 14 is a schematic plane view depiction of an array of the present invention as seen from the step 8 of FIG. 9.

Alternatively, devices may be fabricated with the two photon lithography as shown in FIG. 12f. This process uses the step of two-photon lithography instead of conventional optical lithography to expose or cross-link the selected regions on the organic polymer 190. The unexposed portions of the polymer 190 are subsequently developed as shown in steps g and h, to form the desired patterns such as reservoirs 110, barriers 120, and access windows 250 as shown in the FIG. 11h.

An embodiment similar to the one depicted in FIG. 11 can be formed as a scanning microscope tip with the added functionality of facilitating the transmission of liquids and molecules to the sample that is being probed.

It will be appreciated that the devices and probes of the present invention lend themselves to certain novel methods. To that end, there are methods of delivering a medicament comprise placing a medicament in a fluid, placing the fluid into at least one probe as described herein, and delivering the medicament contained within the fluid into a biological membrane through the nanotube. The biological membrane may be a cell membrane. The medicament to be delivered may comprise protein, hormones, antibiotics, enzymes, or chemical agents. In some embodiments, there is more than one probe being utilized. In such embodiments, the medicament contained within the fluid may be injected into a membrane through more than one probe. Also, the probes in such embodiments may act in parallel during injection.

There are also methods of monitoring the fluidic interactions of an analyte or molecule or between molecules in suspension and molecules immobilized to the nanotube's wall comprise placing the analytes or molecules in a fluid, placing the fluid into a device as described in the present disclosure, and observing the fluidic interactions of said analyte within the nanotube. There are also embodiments for monitoring the interactions of an analyte wherein the fluid is placed into an array comprising more than one probe and more than one probe is located on the same substrate. The diameters of the nanotubes in such embodiments may be the same or different. The functionalization of each nanotube may also be the same or different in the probes in array embodiments. In some embodiments, the methods include a step where the fluid is caused to flow from one reservoir to another reservoir or through a membrane. The flow may be caused by electroosmosis or electrophoresis.

Ionic current measurements through embodiments of the present invention have been carried out, and the present invention has utility as a highly sensitive Coulter counter. The experimental observations of the ion transmission and the particle translocation provide evidence that the hybrid fabrication methods of some embodiments provide a well-functioning nanotube based-fluidic device that can be used as a high sensitivity particle counter. Furthermore, the disclosed devices and methods should allow one to position multiple nanotubes with different diameters on the same substrate facilitating massive parallel processing, and extending the technique to nanotubes of molecular dimensions should also be feasible.

The observing steps may be performed via electron microscopy. Observation may also be done using optical or fluorescent microscopy. For optical microscopy, the nanotube confines a minute quantity of labeled analytes that can be observed with minimal interference. The fluidic interactions that may be observed comprise the effects of the analyte or molecule on an ionic current, the size and velocity of the analyte or molecule. Also, the resonance frequency, the electrical resistance, or impedance of the nanotube may be observed. The analyte or molecule may also comprise a drug to be screened or tested. A vacuum may also be applied to the device in some method embodiments.

The nanotubes used in the embodiments of the present invention may be amorphous, multi-walled, or single walled. The physical properties of the nanotube may be modified by chemical or thermal treatment. The walls of the nanotubes may be unmodified or functionalized with ligands or immobilized ligands. The nanotubes may also be electrically charged. A plurality of nanotubes with similar or different diameters and functionalization may be integrated into some embodiments. Groups of nanotubes may communicate with a single reservoir or each nanotube may communicate with an individual reservoir.

Analytes or molecules transmitted within the nanotube may also affect a nanotube's properties. As a result, the mechanical, optical, or electrical properties of the nanotube may be observed in some methods of the present invention. These properties include mass, stiffness, elastic properties, and electric properties. A nanotube's inner wall may also be functionalized to selectively bind or adsorb specific target analytes or molecules. Since the nanotube wall thickness is small, the presence of target analytes within the nanotube and the binding of analytes to the nanotube walls can be sensed by monitoring the wall's mechanical properties such as the natural frequency of the nanotube vibrations or the electrical properties such a electrical resistance and impedance. Adsorbed analytes or molecules may also affect the nanotube wall's optical properties and the electroosmotic velocity of fluids inside the nanotube. The interactions between molecule in suspension and those attached to the nanotube wall may also be observed.

EXAMPLE 1

Figure 4:
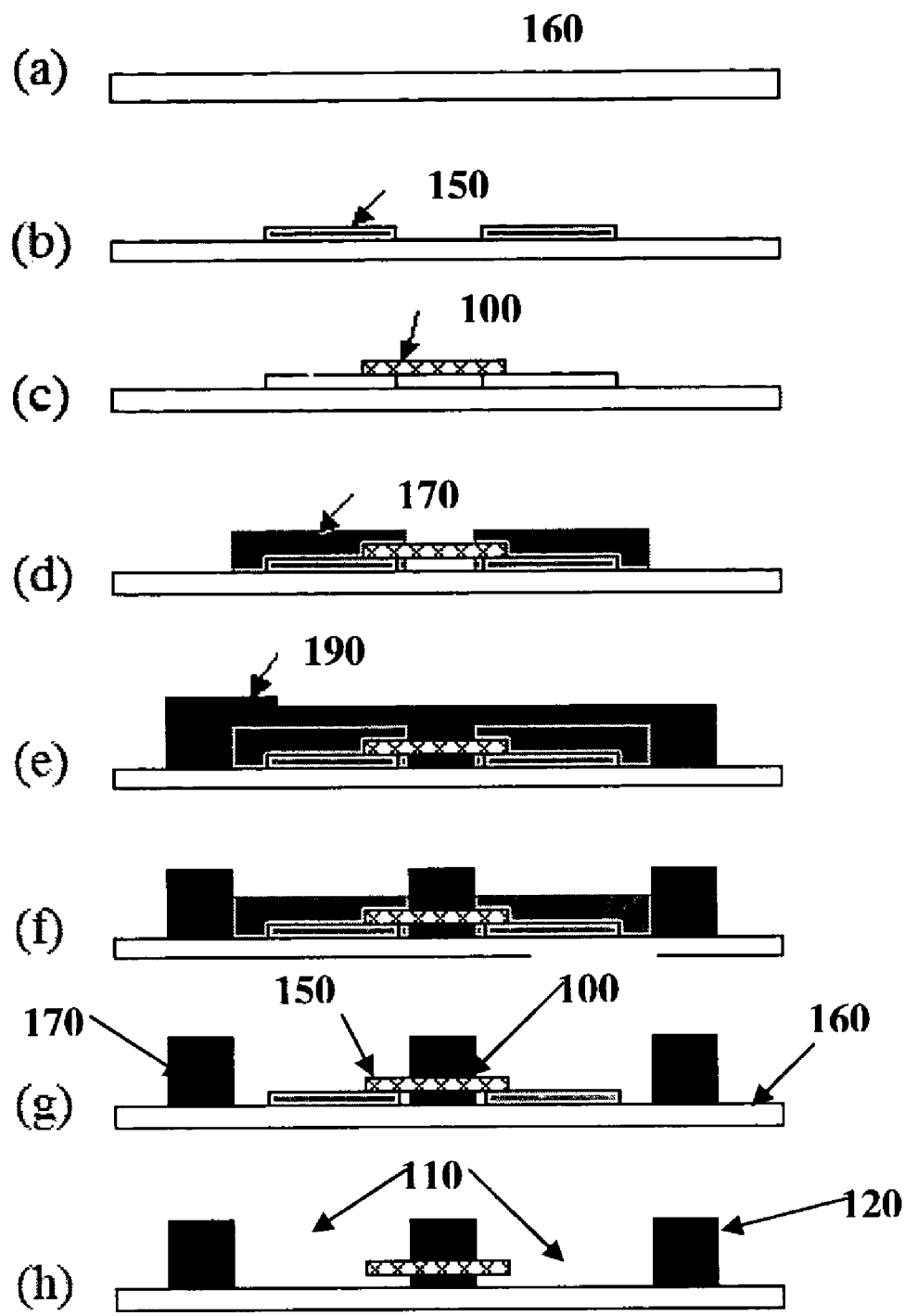
FIG. 4 illustrates steps that may be used in constructing an embodiment of the present invention.

Methods of making some embodiments of the disclosed devices are depicted in FIG. 4. The device fabrication starts with a Si substrate (FIG. 4a). Two electrodes, formed of an evaporated 100-nm-thick Au with a 10-nm-thick NiCr adhesion layer, are patterned on the substrate using standard photolithographic techniques including the process of wet etching of Au and NiCr layers (FIG. 4b). The electrodes-patterned substrate is treated with oxygen plasma (300W, 3 min, Technics—PE11-A) to remove organic contaminants. A carbon nanotube is (FIG. 4c) between the electrodes with a dielectrophoresis assembly method. The dielectrophoresis assembly process consists of positioning a drop laden with a dilute solution (2-isoprophyl alcohol) of template-grown carbon nanotubes on top of the electrodes, and applying AC (10V, 1 MHz) electric field across the electrodes. The nanotubes were polarized and migrate to bridge the gap across the electrodes. Once a nanotube was placed at a desired location, the nanotube's ends are capped by patterning of sacrificial layer (FIG. 4d), formed with a positive photoresist (Shipley Microposit S1813), using standard photolithographic techniques. Then, photolithographic processes utilizing SU-8 photoresist (MichoChem SU-8 2050) are used to construct the necessary plumbing to facilitate liquid flow into and out of the nanotube. The SU-8 is spun at 3000 rpm (FIG. 4e) and patterned to open the reservoirs and to form the barrier structure (nominally 50 μm in height) (FIG. 4f). A hydrofluoric acid treatment is applied between steps d and e to promote the adhesion of SU-8 to the substrate. Sacrificial layers are removed, using a solvent such as a SU-8 developer and acetone, to expose the nanotube's ends (FIG. 4g). The hybrid method renders the barrier structure that separates the two reservoirs and prevents fluid leakage between them while holding the nanotube in position.

EXAMPLE 2

Figure 8:
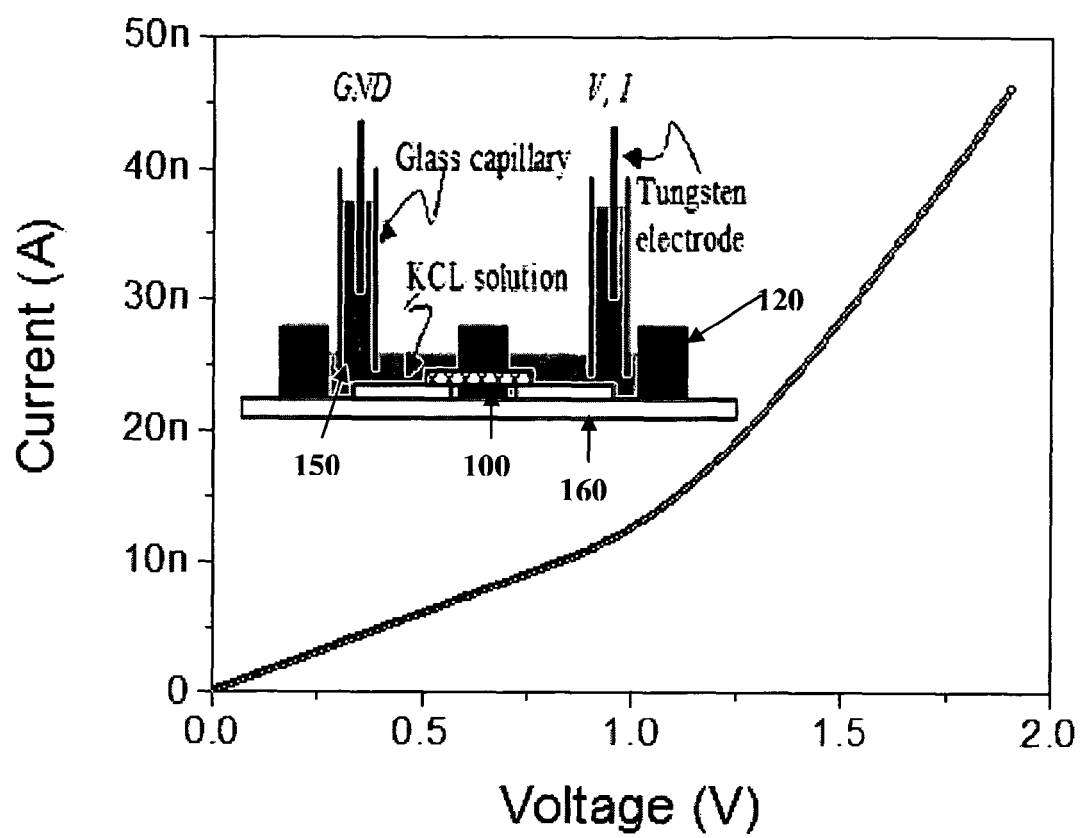
FIG. 8 is the ionic current-voltage curve measurement through the nanotube channel after filling the nanotube with a 0.1 M KCl electrolyte solution. The inset is a schematic of the experimental set-up of an embodiment of the invention.

To demonstrate that the nanotube device can be used to transport ions in aqueous solutions, the nanotubes were filled with a 0.1 M KCl electrolyte solution and measured the current-voltage characteristics. Shown in the FIG. 8 inset is a schematic of the experimental set-up. Tungsten electrodes were submerged in the electrolyte solution inside the glass capillaries that were mounted to either side of the reservoirs. One electrode was held at a ground potential while potential difference was applied through another electrode. An HP 4145B parameter analyzer provided a linear voltage sweep at the rate of 5 mV/s and recorded the corresponding current. FIG. 8 shows ionic current (I) as a function of the potential difference (V) across the driving electrodes. The ionic current across the nanotube below 1V varies linearly as a function of the potential difference applied across the nanotube. The ionic current through a single carbon nanotube, filled with a KCL solution, increases linearly with the potential difference up to the applied voltages of 1V and 0.5V, respectively. Assuming that the current below 1V is carried solely by the ions in the electrolyte solution, ionic current across the nanotube (below 1V) can be described by $I=\sigma\pi d^2 V/4l$, where $\sigma$ is the bulk electrolyte conductivity, d is the nanotube diameter, and l is the nanotube length. This equation can be used to evaluate the geometric parameters of the nanotube. The calculated nanotube diameter is 600 nm with $\sigma=1.29\times10^{-2}\,\Omega^{-1}\,cm^{-1}$ for the 0.1 M KCl solution and the measured nanotube length of 32 μm. This diameter is in qualitative agreement with the nanotube diameter of about 500 nm measured from the optical image of the nanotube device.

The I-V curve of the nanotube device (FIG. 8) exhibits a noticeable change in the ionic conductivity at ~1 V with linear increase in the current response when the potential difference between the two electrodes is larger than 1 V.

EXAMPLE 3

Figure 5:
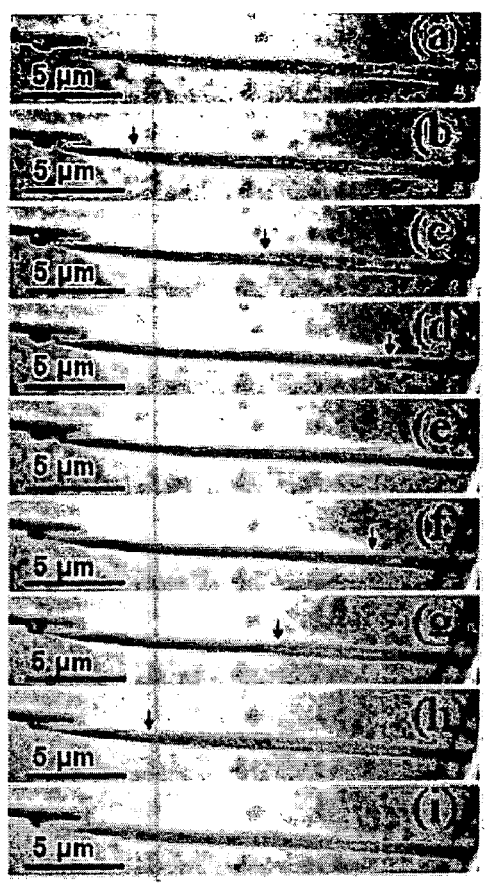
FIG. 5 shows a sequence of transport of liquid ethylene glycol in a nanotube with the liquid vapor interface indicated by vertical black arrows.
Figure 6:
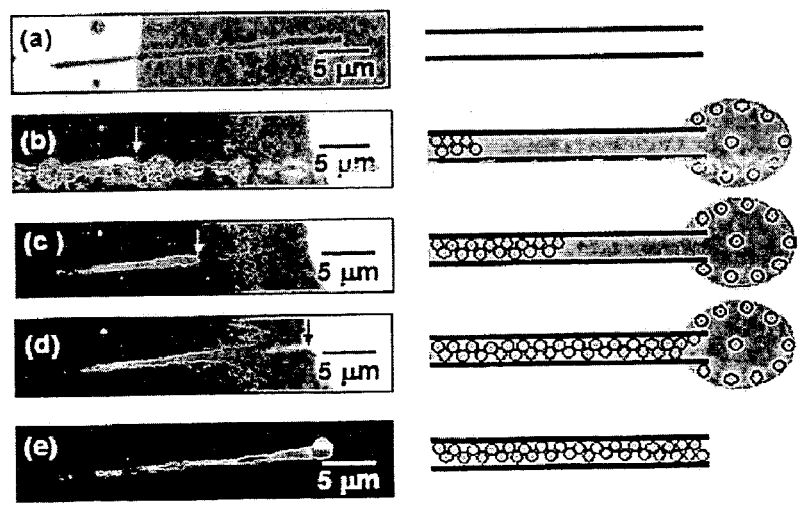
FIG. 6 shows a transport sequence with nanoparticles inside a nanotube with the nanoparticles indicated by vertical white arrows.

Experimental data demonstrates both the transport of fluid inside a carbon nanotube and the feasibility of observing the liquid motion. The motion of the fluid in FIG. 5 and nanoparticles in FIG. 6 inside the nanotube was detected, respectively, by optical microscopy and fluorescence microscopy. FIG. 5 shows a sequence of transport of liquid ethylene glycol in a nanotube with a length of 22 μm and a diameter of about 500 nm. The entire nanotube is filled up by liquid condensation within 3.4 s. The location of the liquid-vapor interface is indicated with a vertical arrow in FIG. 6. The empty part of the nanotube appears as a set of two closely spaced, parallel lines formed by the nanotube's wall with a light-colored medium between them. The liquid-filled part of the nanotube appears dark. The liquid-air interface started to recede from the right end side of the nanotube while the other liquid-air interface remained pinned to the left end side (FIG. 6(a)-(e)). The evaporation process lasted about 4.7 s. The fluorescence microscope images in FIG. 6(b) to 6(d) show the nanotube at 10 s, 20 s, and at 40 s, after the nanotube was brought into contact with a liquid drop laden with fluorescent particles. FIG. 6(a) shows an optical image of a nanotube, 29 μm in length, 500 nm in diameter, and 15 nm in wall thickness. The portion of the nanotube packed with the 50 nm diameter fluorescence beads appears as a segment of a bright line on the fluorescence microscope. The rest of the nanotube appears dark. As the particles accumulate, the bright line grows to include the entire nanotube length of 29 um in 40 seconds. The location of the stacked particles'-liquid interface is indicated with vertical arrows in FIG. 6. The schematic depiction of the particle packing is shown on the right-hand side of FIG. 6. The particle filling process is reproducible.

What is claimed:
1. An analytical device comprising:
two reservoirs capable of fluid containment; and
at least one nanotube placing said reservoirs in fluid communication with one another, a portion of the exterior of the at least one nanotube being exposed to the environment exterior to the reservoirs,
at least a portion of the lumen of at least one nanotube being observable by electron or ion-beam microscopy.
2. The device of claim 1 wherein said nanotube comprises carbon, silicon, silicon oxide, semiconductor, metal, or glass.
3. The device of claim 1 wherein said nanotube is amorphous, multi-walled, or single walled.
4. The device of claim 1 wherein said reservoirs are capped.
5. The device of claim 4 wherein said reservoirs are capped with polymer, semiconductor, glass, or metal.
6. The device of claim 1 wherein said reservoirs comprise electrodes.
7. The device of claim 1 wherein the properties of said nanotube are modified by chemical or thermal treatment.
8. The device of claim 1 wherein the wall of said nanotube is functionalized with immobilized ligands.
9. The device of claim 1 wherein said reservoirs hold fluid.
10. The device of claim 9 wherein said fluid comprises a liquid, a suspension, an emulsion, a gas, or any combination thereof.
11. The device of claim 10, wherein said suspension comprises a fluorescent bead, a functionalized bead, an unfunctionalized bead, a magnetic bead, a macromolecule, or any combination thereof.
12. The device of claim 11, wherein said macromolecule comprises a nucleic acid, an enzyme, a dendrimer, a protein, or any combination thereof.
13. The device of claim 1 wherein said barrier structure comprises polymer, silicon, or silicon dioxide.
14. The analytical device of claim 1, wherein the portion of the exterior of the at least one nanotube being exposed to the environment exterior to the reservoirs resides exterior to both reservoirs.
15. The analytical device of claim 1, wherein at least a portion of the at least one nanotube extends into the interior of at least one reservoir.
16. An analytical device comprising:
a substrate;
a barrier structure,
   at least a portion of the barrier structure extending from the substrate so as to define at least two reservoirs for fluid containment,
at least one nanotube disposed within the barrier structure between said reservoirs such that the ends of the at least one nanotube are in fluid communication with said reservoirs,
at least a portion of the at least one nanotube extending into at least one of the reservoirs,
and the device being configured such that the lumen of the at least one nanotubes is observable through the barrier structure by an electron, ion-beam, or optical microscope.
17. The analytical device of claim 16 wherein more than one nanotube is between two reservoirs with the ends of said nanotube in fluid communication with said reservoirs.
18. The analytical device of claim 16 wherein more than one nanotube has an end in fluid communication with a reservoir.
19. The analytical device of claim 16 wherein said nanotube comprises carbon, silicon, silicon oxide, semiconductor, metal, or glass.

20. The analytical device of claim 16 wherein said nanotube is amorphous, multi-walled, or single walled.

21. The analytical device of claim 16 wherein said reservoirs are capped.

22. The analytical device of claim 21 wherein said reservoirs are capped with polymer, semiconductor, glass, or metal.

23. The analytical device of claim 16 wherein said reservoirs comprise electrodes.

24. The analytical device of claim 16 wherein the properties of said nanotube are modified by chemical or thermal treatment.

25. The analytical device of claim 16 wherein the wall of said nanotube is functionalized with immobilized ligands.

26. The analytical device of claim 16 wherein at least one of said reservoirs holds fluid.

27. The analytical device of claim 26 wherein the fluid within at least one of said reservoirs comprises a liquid, a suspension, an emulsion, a gas, or any combination thereof.

28. The analytical device of claim 27 wherein said suspension comprises a fluorescent bead, a functionalized bead, an unfunctionalized bead, a magnetic bead, a macromolecule, or any combination thereof.

29. The analytical device of claim 28 wherein said macromolecule comprises a nucleic acid, an enzyme, a dendrimer, a protein, or any combination thereof.

30. The analytical device of claim 16 wherein said barrier structure comprises polymer, silicon, or silicon dioxide.

31. The analytical device of claim 17 wherein at least one nanotube differs from the remaining nanotubes in diameter, wall thicknesses, or functionalization.

32. The analytical device of claim 16, wherein at least a portion of the nanotube is in physical contact with the substrate.

33. The analytical device of claim 16, wherein at least a portion of the nanotube is not in physical contact with the substrate.

34. The analytical device of claim 16, wherein the at least one nanotubes is at least about 5 micrometers in length.

35. A probe comprising:
a substrate;
a barrier structure defining one reservoir for fluid containment; and
a nanotube having an opening proximal to and in fluid communication with said reservoir and at least a portion of the nanotube extending into the interior of the reservoir and a portion of the nanotube extending into the environment exterior to the probe.

36. The probe of claim 35 wherein said nanotube comprises carbon.

37. The probe of claim 35 wherein said nanotube is amorphous, multi-walled, or single-walled.

38. The probe of claim 35 wherein said reservoir is capped.

39. The probe of claim 38 wherein said reservoir is capped with polymer, semiconductor, glass, or metal.

40. The probe of claim 35 wherein said reservoir comprises electrodes.

41. The probe of claim 35 wherein the nanotube properties are modified by chemical or thermal treatment.

42. The probe of claim 35 wherein the wall of said nanotube is functionalized with immobilized ligands.

43. The probe of claim 35 wherein said reservoir holds fluid.

44. The probe of claim 43 wherein said fluid comprises a liquid, a suspension, an emulsion, a gas, or any combination thereof.

45. The probe of claim 44 wherein said suspension comprises a fluorescent bead, a functionalized bead, an unfunctionalized bead, a magnetic bead, a macromolecule, or any combination thereof.

46. The probe of claim 45 wherein said macromolecule comprises a nucleic acid, an enzyme, a dendrimer, a protein, or any combination thereof.

47. The probe of claim 35 wherein said barrier structure comprises polymer, silicon, or silicon dioxide.

48. The probe of claim 35, wherein at least a portion of the nanotube is in physical contact with the substrate.

49. The probe of claim 35, wherein at least a portion of the nanotube is not in physical contact with the substrate.

50. An array, comprising:
a substrate;
barrier structures on said substrate defining reservoirs for fluid containment; and
more than one nanotube having an opening proximal to and in fluid communication with said reservoir and also having a portion that extends into the environment exterior to the array.

51. The array of claim 50 wherein at least one nanotube differs from the remainder of said nanotubes in diameter, wall thickness, or functionalization.

52. The array of claim 50 wherein said nanotubes comprise carbon, silicon, silicon oxide, semiconductor, metal, or glass.

53. The array of claim 50 wherein said nanotubes is amorphous, single walled, or multi-walled.

54. The array of claim 50 wherein said reservoirs are capped.

55. The array of claim 50 wherein said reservoirs are capped polymer, glass, semiconductor, or metal.

56. The array of claim 50 wherein said reservoirs comprises electrodes.

57. The array of claim 50 wherein the properties of said nanotubes are modified by chemical or thermal treatment.

58. The array of claim 57 wherein the properties of at least one nanotube differ from the remainder of said nanotubes.

59. The array of claim 50 wherein the walls of at least one nanotube are functionalized with immobilized ligands.

60. The array of claim 50 wherein said reservoirs hold fluid.

61. The array of claim 60 wherein the fluid differs in each probe.

62. The array of claim 60 wherein said fluid comprises a liquid, a suspension, an emulsion, a gas, or any combination thereof.

63. The array of claim 62, wherein said suspension comprises a fluorescent bead, a functionalized bead, an unfunctionalized bead, a magnetic bead, a macromolecule, or any combination thereof.

64. The array of claim 63, wherein said macromolecule comprises a nucleic acid, an enzyme, a dendrimer, a protein, or any combination thereof.

65. The array of claim 50, wherein said barrier structures comprise polymer, silicon, or silicon dioxide.

66. The array of claim 50, wherein at least a portion of the nanotube is in physical contact with the substrate.

67. The array of claim 50, wherein at least a portion of the nanotube is not in physical contact with the substrate.

* * * * *